US012383221B2

(12) United States Patent
Asai et al.

(10) Patent No.: US 12,383,221 B2
(45) Date of Patent: Aug. 12, 2025

(54) BIOLOGICAL SOUND MEASURING DEVICE, BIOLOGICAL SOUND MEASUREMENT SUPPORT METHOD, AND BIOLOGICAL SOUND MEASUREMENT SUPPORT PROGRAM

(71) Applicant: OMRON HEALTHCARE CO., LTD., Muko (JP)

(72) Inventors: Kei Asai, Kyoto (JP); Kenji Hashino, Kyoto (JP); Naoto Ohgami, Kyoto (JP); Naoki Matsumoto, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 1081 days.

(21) Appl. No.: 17/060,169

(22) Filed: Oct. 1, 2020

(65) Prior Publication Data

US 2021/0015444 A1 Jan. 21, 2021

Related U.S. Application Data

(63) Continuation of application No. PCT/JP2019/015679, filed on Apr. 10, 2019.

(30) Foreign Application Priority Data

Apr. 18, 2018 (JP) ................................. 2018-080188

(51) Int. Cl.
*A61B 5/00* (2006.01)
*A61B 7/00* (2006.01)
(Continued)

(52) U.S. Cl.
CPC .............. *A61B 7/04* (2013.01); *A61B 5/6843* (2013.01); *A61B 5/7285* (2013.01);
(Continued)

(58) Field of Classification Search
None
See application file for complete search history.

(56) References Cited

U.S. PATENT DOCUMENTS

2001/0014162 A1\* 8/2001 Orten ....................... A61B 7/04
600/528
2012/0059280 A1 3/2012 Horii
(Continued)

FOREIGN PATENT DOCUMENTS

| CN | 102469990 A | 5/2012 |
| CN | 107184231 A | 9/2017 |

(Continued)

OTHER PUBLICATIONS

Official Communication issued in corresponding Chinese Patent Application No. 201980026268.3, mailed on Nov. 25, 2021.
(Continued)

*Primary Examiner* — Etsub D Berhanu
(74) *Attorney, Agent, or Firm* — Keating & Bennett, LLP

(57) ABSTRACT

There is provided a biological sound measuring device that has a member which defines a space to be sealed by a body surface of a living body in a state of being pressed against the body surface, and that measures a biological sound of the living body based on pressure fluctuation in the space. The device includes: a sound generator that generates a sound toward the body surface; a sound measurer that measures a reflected sound of the sound generated by the sound generator; and a controller that determines whether or not a contact state or a contact position of the member with respect to the body surface satisfies a condition necessary for measurement of the biological sound, based on the reflected sound measured by the sound measurer, and that performs notification when it is determined that the condition is not satisfied.

10 Claims, 11 Drawing Sheets

(51) Int. Cl.
  *A61B 7/04*   (2006.01)
  *G08B 21/18*  (2006.01)
  *G10L 25/66*  (2013.01)
  *G16H 10/40*  (2018.01)

(52) U.S. Cl.
  CPC ............ *G08B 21/182* (2013.01); *G10L 25/66* (2013.01); *G16H 10/40* (2018.01); *A61B 7/003* (2013.01)

(56) References Cited

U.S. PATENT DOCUMENTS

| | | |
|---|---|---|
| 2012/0130240 A1 | 5/2012 | Sakamoto et al. |
| 2013/0131465 A1 | 5/2013 | Yamamoto et al. |
| 2013/0338478 A1 | 12/2013 | Hirota et al. |
| 2014/0051969 A1 | 2/2014 | Suzuki |
| 2014/0302473 A1 | 10/2014 | Nakaguchi et al. |
| 2015/0335252 A1* | 11/2015 | Hirota ................ A61B 5/7246 600/407 |
| 2016/0007923 A1 | 1/2016 | Yamamoto |
| 2016/0100817 A1* | 4/2016 | Hussain ................ A61B 7/04 600/528 |
| 2016/0354054 A1 | 12/2016 | Minegishi et al. |
| 2017/0049331 A1 | 2/2017 | Suzuki |
| 2018/0177482 A1 | 6/2018 | Hashino et al. |
| 2020/0289083 A1 | 9/2020 | Ogawa |

FOREIGN PATENT DOCUMENTS

| | | |
|---|---|---|
| JP | 11-508461 A | 7/1999 |
| JP | 2012-024391 A | 2/2012 |
| JP | 2012-152377 A | 8/2012 |
| JP | 2012-231979 A | 11/2012 |
| JP | 2012-247513 A | 12/2012 |
| JP | 2015-020030 A | 2/2015 |
| JP | 2016-007412 A | 1/2016 |
| JP | 2017-000198 A | 1/2017 |
| JP | 2017-074190 A | 4/2017 |
| JP | 2017-170112 A | 9/2017 |
| WO | 97/01768 A2 | 1/1997 |
| WO | 2011/114669 A1 | 9/2011 |
| WO | 2012/114729 A1 | 8/2012 |
| WO | 2014/156913 A1 | 10/2014 |
| WO | 2016/143116 A1 | 9/2016 |

OTHER PUBLICATIONS

Official Communication issued in International Patent Application No. PCT/JP2019/015679, mailed on Jul. 16, 2019.

\* cited by examiner

BIOLOGICAL SOUND MEASURING DEVICE, BIOLOGICAL SOUND MEASUREMENT SUPPORT METHOD, AND BIOLOGICAL SOUND MEASUREMENT SUPPORT PROGRAM

CROSS-REFERENCE TO RELATED APPLICATIONS

This application is a continuation of PCT application No. PCT/JP2019/015679, which was filed on Apr. 10, 2019 based on Japanese Patent Application No. 2018-080188 filed on Apr. 18, 2018, the contents of which are incorporated herein by way of reference.

BACKGROUND

The present invention relates to a biological sound measuring device that is to be brought into contact with a body surface of a living body so as to be used, a biological sound measurement support method and a program that support measurement of a biological sound performed by the biological sound measuring device.

There has been known a device that uses a microphone to extract, as an electrical signal, a biological sound such as a respiratory sound as a sound of an airflow for ventilating the airway and the alveoli, an adventitious sound that is an abnormal sound during breathing which is generated in pathological conditions such as wheezing or pleural friction, or a cardiac sound.

Patent Literature 1 discloses a respiratory measuring device that detects a respiratory sound, and discloses a point that a light source disposed inside a sound collecting member and a photodetector provided outside the sound collecting member are used to determine attachment of the measuring device.

Patent Literature 2 discloses a biological sound collecting device, and discloses a point that a contact sensor, which detects contact between a sound collecting unit and a living body surface, is used to determine a contact state between the sound collecting unit and the living body surface.

Patent Literature 3 discloses a biological sound examination device, and discloses a point that whether or not a position of a biological sound measuring unit is appropriate is determined by signal processing performed on a detected biological sound.

Patent Literature 4 discloses that an optimum wearing position of a device is determined by comparing a plurality of sounds measured at different positions by one microphone, or by comparing a plurality of sounds measured by a plurality of microphones attached at different positions.

Patent Literature 1: JP-A-2017-74190
Patent Literature 2: JP-A-2015-20030
Patent Literature 3: WO-A1-11/114669, pamphlet
Patent Literature 4: JP-A-2012-24391

For a biological sound measuring device that measures a biological sound necessary for diagnosis of a living body, improvement of measurement accuracy of the biological sound is required. In order to improve the measurement accuracy of the biological sound, a contact state between the biological sound measuring device and a body surface of the living body, or a position on the body surface with which the biological sound measuring device is to be in contact is needed to satisfy a predetermined condition.

The devices disclosed in Patent Literatures 1 and 2 determine whether or not the contact state with the body surface is good by using a light source and a photodetector, or a contact sensor. However, with the photodetector or the contact sensor, it is difficult to accurately determine the contact state.

The devices disclosed in Patent Literatures 3 and 4 determine whether or not the positions of the devices are optimal by analyzing measurement sounds. However, it is difficult to accurately perform this determination only by analyzing the measurement sounds.

SUMMARY

The present invention has been made in view of the above circumstances, and an object thereof is to provide a biological sound measuring device, a biological sound measurement support method, and a biological sound measurement support program, which are capable of determining with high accuracy whether or not one or both of a contact state with a body surface of a living body and a contact position of the device with respect to the body surface satisfy a condition necessary for measuring a biological sound and which are capable of improving measurement accuracy of the biological sound.

According to one aspect of the present invention, there is provided a biological sound measuring device that has a member which defines a space to be sealed by a body surface of a living body in a state of being pressed against the body surface, and that measures a biological sound of the living body based on pressure fluctuation in the space. The device includes:

a sound generator that is disposed in the space of the member and that generates a sound toward the body surface; a sound measurer that is disposed in the space of the member and that measures a reflected sound of the sound generated by the sound generator; and a controller that determines whether or not a contact state or a contact position of the member with respect to the body surface satisfies a condition necessary for measurement of the biological sound, based on the reflected sound measured by the sound measurer, and that performs notification when it is determined that the condition is not satisfied.

According to other aspect of the present invention, when an intensity of the reflected sound measured by the sound measurer is lower than a threshold set in advance, the controller determines that the contact state does not satisfy the condition.

According to other aspect of the present invention, when the intensity of the reflected sound is equal to or greater than the threshold, and further when a difference between a generation timing of the sound by the sound generator and a measurement timing of the reflected sound of the sound which is measured by the sound measurer is within a first range set in advance and the intensity of the reflected sound is within a second range set in advance, the controller determines that the contact position does not satisfy the condition.

According to other aspect of the present invention, when the intensity of the reflected sound is equal to or greater than the threshold, and further when the difference between the generation timing of the sound by the sound generator and the measurement timing of the reflected sound of the sound which is measured by the sound measurer is outside the first range or the intensity of the reflected sound is outside the second range, the controller determines that the contact state and the contact position satisfy the condition.

According to other aspect of the present invention, when a difference between a generation timing of the sound by the sound generator and a measurement timing of the reflected sound of the sound which is measured by the sound measurer is within a first range set in advance and an intensity of the reflected sound is within a second range set in advance, the controller determines that the contact position does not satisfy the condition.

According to other aspect of the present invention, the biological sound measuring device further includes: a sound measuring element that is disposed in the space of the member and that measures a sound in a frequency range lower than the frequency range of the sound generated by the sound generator. When it is determined that one or both of the contact state and the contact position satisfy the condition, the controller stores, as the biological sound, a sound in a predetermined frequency range of sounds to be measured by the sound measuring element.

According to other aspect of the present invention, the sound measurer measures the sound generated by the sound generator and a sound in a frequency range lower than the frequency range of the sound generated by the sound generator. When it is determined that one or both of the contact state and the contact position satisfy the condition, the controller stores, as the biological sound, a sound that is different from the sound generated by the sound generator and that is in a predetermined frequency range, of sounds to be measured by the sound measurer.

According to other aspect of the present invention, the predetermined frequency range is 10 Hz or more and 1.5 kHz or less.

According to other aspect of the present invention, the sound generator is formed along an inner wall that defines the space of the member. A sound generating surface of the sound generator is inclined in a direction away from the body surface with respect to a plane perpendicular to a pressing direction of the member.

According to other aspect of the present invention, there is provided a biological sound measurement support method for supporting measurement of a biological sound performed by a biological sound measuring device. The biological sound measuring device includes: a member that defines a space to be sealed by a body surface of a living body in a state of being pressed against the body surface; a sound generator that is disposed in the space of the member and that generates a sound toward the body surface; and a sound measurer that is disposed in the space of the member and that measures at least a reflected sound of the sound generated by the sound generator. The biological sound measuring device measures the biological sound of the living body based on pressure fluctuation in the space. The biological sound measurement support method includes: a step of determining whether or not a contact state or a contact position of the member with respect to the body surface satisfies a condition necessary for measurement of the biological sound, based on the reflected sound measured by the sound measurer, and performing notification when it is determined that the condition is not satisfied.

According to other aspect of the present invention, there is provided a storage medium which stores a biological sound measurement support program for supporting measurement of a biological sound performed by a biological sound measuring device. The biological sound measuring device includes: a member that defines a space to be sealed by a body surface of a living body in a state of being pressed against the body surface; a sound generator that is disposed in the space of the member and that generates a sound toward the body surface; and a sound measurer that is disposed in the space of the member and that measures at least a reflected sound of the sound generated by the sound generator. The biological sound measuring device measures the biological sound of the living body based on pressure fluctuation in the space. The biological sound measurement support program causes a computer to perform a step of: determining whether or not a contact state or a contact position of the member with respect to the body surface satisfies a condition necessary for measurement of the biological sound, based on the reflected sound measured by the sound measurer, and performing notification when it is determined that the condition is not satisfied.

Figure 1:
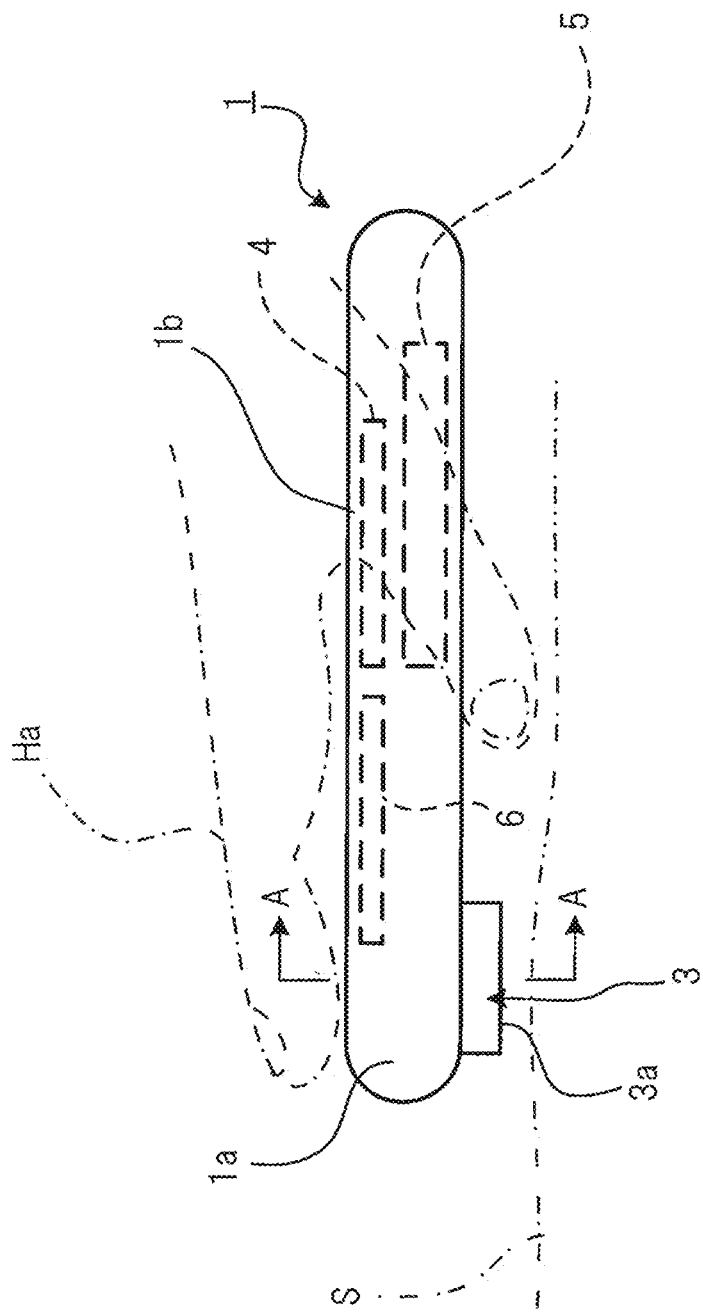
FIG. 1 is a side view illustrating a schematic configuration example of a biological sound measuring device 1 as an embodiment of a biological sound measuring device of the present invention.

DESCRIPTION OF EMBODIMENTS (Outline of Biological Sound Measuring Device of Embodiment)

First, an outline of an embodiment of a biological sound measuring device of the present invention will be described. The biological sound measuring device according to the embodiment measures a pulmonary sound (a respiratory sound and an adventitious sound) as an example of a biological sound by a measuring unit with the measuring unit pressed between ribs of a person, and when it is determined that wheezing as the adventitious sound is included in a measured sound, the biological sound measuring device notifies that. By this way, support is given in determination of whether to give medicine to the subject, determination of whether to bring the subject to a hospital, or diagnosis by a doctor for the subject.

The biological sound measuring device according to the embodiment includes a measuring unit having a housing that accommodates a sound measuring element for measuring a pulmonary sound. An internal space for accommodating the sound measuring element in the housing is sealed by a body surface, and the biological sound measuring device measures a pulmonary sound of a living body by measuring pressure fluctuation in the space in this state with the sound measuring element.

In the housing, a sound generator that generates a test sound toward the body surface and a sound measurer that measures a reflected sound of the test sound are accommodated. In a state where the measuring unit is in contact with the body surface of the living body, a test sound is emitted from the sound generator toward the body surface, and a reflected sound of the test sound is measured by the sound measurer.

When a hard biological tissue such as bone is present below the body surface that the measuring unit is in contact with, for example, an intensity of the reflected sound of the test sound is increased. Further, a time period from the time when the test sound is generated to the time when the reflected sound thereof is measured varies depending on a depth at which the bone is present. Further, when there is, for example, a gap between the measuring unit and the body surface and sealing state of the space of the housing is incomplete, the intensity of the reflected sound is lower as compared with that in a case where the sealing state is complete.

The biological sound measuring device of the embodiment uses a measurement result of the reflected sound to determine whether or not the contact state between the measuring unit and the body surface and the contact position of the measuring unit satisfy a condition necessary for measurement of the pulmonary sound. When the condition is not satisfied, notification is performed to prompt a change in a way of pressing the measuring unit against the body surface or a change in a position for pressing the measuring unit, thereby supporting accurate measurement of the pulmonary sound. Hereinafter, a specific configuration example of the biological sound measuring device of the embodiment will be described.

Embodiment

FIG. 1 is a side view illustrating a schematic configuration example of a biological sound measuring device 1 as an embodiment of the biological sound measuring device of the present invention.

As illustrated in FIG. 1, the biological sound measuring device 1 includes a main body 1b formed of a housing made of resin, metal, or the like, and a head portion 1a is provided on one end side of the main body 1b.

Inside the main body 1b, a controller 4 that performs overall control of the whole, a battery 5 that supplies a voltage required for operation, and a display unit 6 that displays an image by a liquid crystal display panel, an organic electro luminescence (EL) display panel or the like are provided.

The controller 4 includes a central processing unit (CPU), a random access memory (RAM), a read only memory (ROM), and the like, and controls hardware of the biological sound measuring device 1 in accordance with a program. Programs including a biological sound measurement support program are stored in the ROM of the controller 4.

The head portion 1a is provided with the measuring unit 3 protruding toward one side (a lower side in FIG. 1) in a direction substantially orthogonal to a longitudinal direction of the biological sound measuring device 1. At a tip end of the measuring unit 3, a pressure receiving portion 3a that is to be brought into contact with a body surface S of a living body, which is a subject, to receive a pressure from the body surface S, is provided.

In using the biological sound measuring device 1, a user places, for example, an index finger of his/her hand Ha on a back surface of the measuring unit 3 in the head portion 1a, and presses the pressure receiving portion 3a of the measuring unit 3 against the body surface S with the index finger. Hereinafter, a direction in which the pressure receiving portion 3a is pressed against the body surface S is referred to as a pressing direction (a direction from an upper side to a lower side in FIG. 1).

Figure 2:
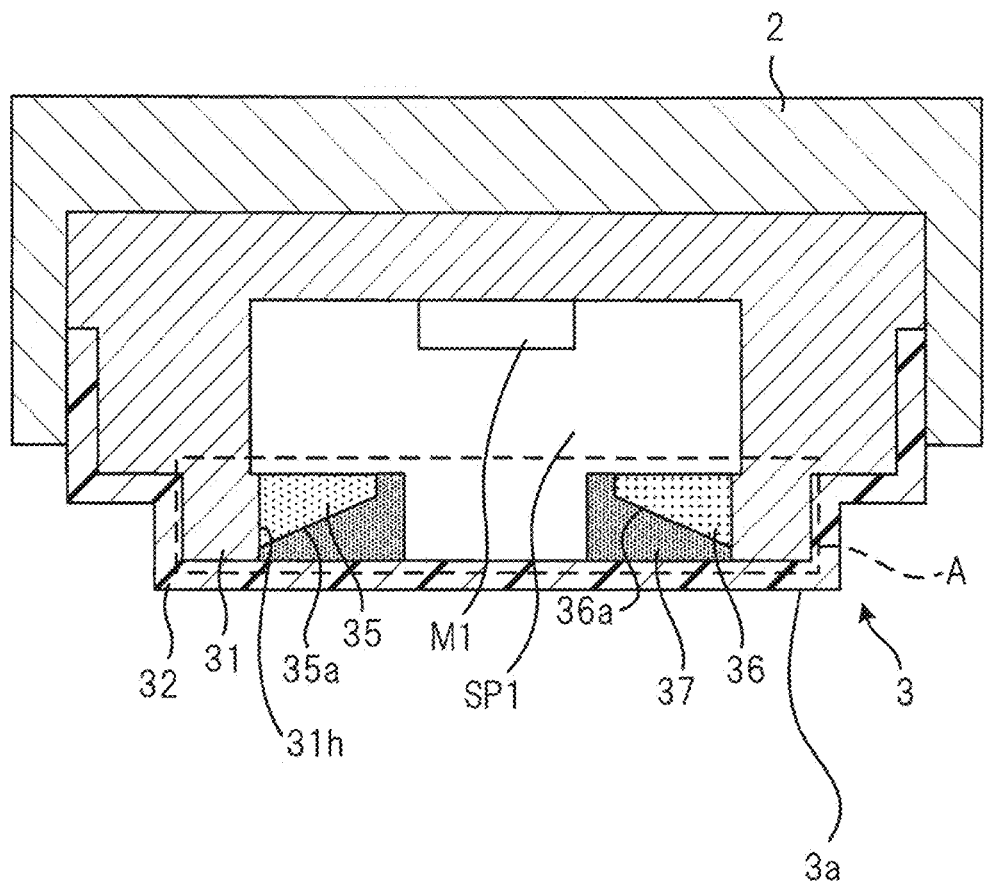
FIG. 2 is a schematic cross-sectional view of the biological sound measuring device 1 taken along a line A-A in FIG. 1.

FIG. 2 is a schematic cross-sectional view of the biological sound measuring device 1 taken along a line A-A in FIG. 1.

The measuring unit 3 includes a bottomed cylindrical housing 31 as a member that forms an accommodation space SP1 to be sealed by the body surface S in a state of being pressed against the body surface S, a sound measuring element M1 that measures a sound generated in the accommodation space SP1 of the housing 31, a sound generator 35, a sound measurer 36, an acoustic impedance matching layer 37, and a housing cover 32 that closes the accommodation space SP1 from the outside and covers the housing 31.

The measuring unit 3 is fitted into an opening portion formed in a housing 2 constituting the head portion 1a, with a part of the housing cover 32 being exposed, and is fixed to the housing 2.

A tip end portion of the part of the housing cover 32, which is exposed from the housing 2, is a flat surface or a curved surface, and this flat surface or curved surface constitutes the pressure receiving portion 3a of FIG. 1.

An outer shape of the housing 31 is a substantially convex shape directed in a lower direction in FIG. 2, and is made of a material having higher acoustic impedance than air and having higher rigidity, such as a resin or a metal. The housing 31 is made of a material that reflects a sound in a measurement frequency band of the sound measuring element M1 so that the sound is not transmitted from the outside into the accommodation space SP1 in a state of being in contact with the body surface S.

The housing cover 32 is a bottomed cylindrical member, and a shape of a hollow portion thereof substantially coincides with a shape of an outer wall of the housing 31.

The housing cover 32 is made of a material having acoustic impedance close to that of a human body, air, or water, and having flexibility and good biocompatibility. As a material of the housing cover 32, for example, silicon, an elastomer, or the like is used.

The sound measuring element M1 is configured to measure a pulmonary sound to be measured by the biological sound measuring device 1, and is configured with, for example, a micro electro mechanical systems (MEMS) microphone or a capacitance-type microphone that measures a sound in a frequency band (for example, a frequency range of 10 Hz or more and 10 kHz or less) wider than a frequency range of pulmonary sound (generally, 10 Hz or more and 1.5 kHz or less).

The sound measuring element M1 is electrically connected to the controller 4 illustrated in FIG. 1 by a lead wire or the like (not illustrated), and transmits information on a measured sound to the controller 4.

The sound generator 35 is a device that generates a sound toward the body surface S, and in the present embodiment, is configured with an ultrasonic transducer having one or a plurality of piezoelectric elements that convert an electrical signal into a pressure vibration wave. A frequency of the sound generated by the sound generator 35 is a frequency (for example, several MHz), higher than those in the frequency range of pulmonary sound (generally, 10 Hz or more and 1.5 kHz or less).

The sound generator 35 is electrically connected to the controller 4 by a lead wire or the like (not illustrated), and generates a sound in accordance with an instruction from the controller 4.

The sound measurer 36 is a device that measures a reflected sound obtained when the sound generated by the sound generator 35 is reflected in the living body, and in the present embodiment, is configured with an ultrasonic transducer having one or a plurality of piezoelectric elements that convert a pressure vibration wave into an electrical signal. A frequency range of the sound that the sound measurer 36 can measure coincides with a frequency range of the sound generated by the sound generator 35.

The sound measurer 36 is electrically connected to the controller 4 by a lead wire or the like (not illustrated), and a signal of the sound measured here is transmitted to the controller 4.

The acoustic impedance matching layer 37 is joined to a sound generating surface 35a on which the piezoelectric element of the sound generator 35 is formed and to a sound measuring surface 36a on which the piezoelectric element of the sound measurer 36 is formed, and is a layer for matching impedance of the body surface S with impedance of the sound generator 35 and the sound measurer 36.

The acoustic impedance matching layer 37 is made of a material having acoustic impedance close to that of a human body, air, or water, and having flexibility and good biocompatibility. As a material of the acoustic impedance matching layer 37, for example, silicon, an elastomer, or the like is used.

Figure 3:
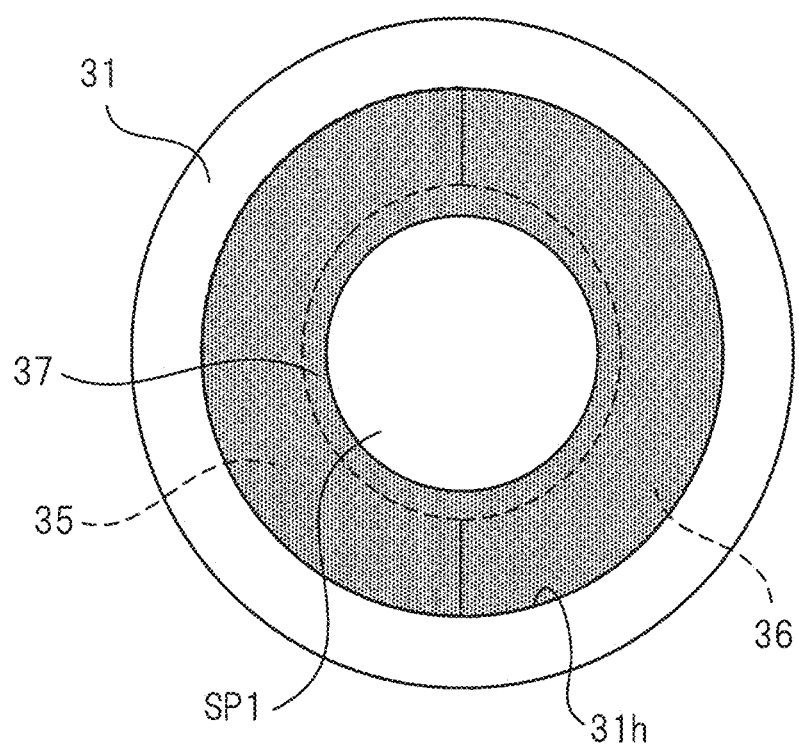
FIG. 3 is a schematic view of a portion of a range A indicated by a broken line, of the measuring unit 3 illustrated in FIG. 2, as viewed from a pressing direction.
Figure 4:
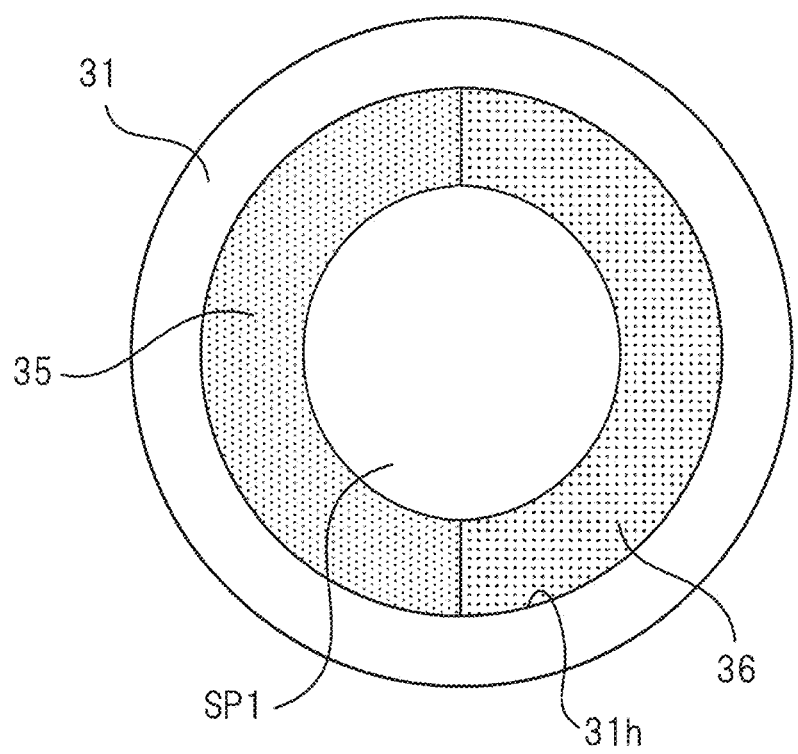
FIG. 4 is a view with illustration of an acoustic impedance matching layer 37 in FIG. 3 being omitted.

FIG. 3 is a schematic view of a portion of a range A indicated by a broken line, of the measuring unit 3 illustrated in FIG. 2, as viewed from the pressing direction. FIG. 4 is a view with illustration of the acoustic impedance matching layer 37 in FIG. 3 being omitted.

As illustrated in FIGS. 2 and 3, at an end portion 31h of an inner wall defining the accommodation space SP1 of the housing 31, which is on the body surface S side, the acoustic impedance matching layer 37 whose planar shape along the end portion 31h is an annular shape, is formed.

Further, as illustrated in FIGS. 2 and 4, the sound generator 35 whose planar shape along the end portion 31h is a semi-annular shape and the sound measurer 36 whose planar shape along the end portion 31h is a semi-annular shape, are fixed to the end portion 31h of the housing 31.

As illustrated in FIG. 2, the sound generating surface 35a of the sound generator 35 is inclined in a direction away from the body surface S with respect to a plane perpendicular to the pressing direction, and an end portion thereof on the end portion 31h side is located closer to the body surface S than an end portion thereof on a center side of the accommodation space SP1. Similarly, the sound measuring surface 36a of the sound measurer 36 is inclined in a direction away from the body surface S with respect to the plane perpendicular to the pressing direction, and an end portion thereof on the end portion 31h side is located closer to the body surface S than an end portion thereof on the center side of the accommodation space SP1. An angle formed by the sound generating surface 35a and the plane perpendicular to the pressing direction is preferably the same as an angle formed by the sound measuring surface 36a and the plane perpendicular to the pressing direction.

A part of the end portion of the accommodation space SP1 on the body surface S side is blocked by the sound generator 35, the sound measurer 36, and the acoustic impedance matching layer 37. Therefore, a biological sound transmitted from the living body in a state where the measuring unit 3 is pressed against the body surface S, is transmitted to the sound measuring element M1 through a portion of the accommodation space SP1 which is surrounded by the sound generator 35, the sound measurer 36, and the acoustic impedance matching layer 37.

At the time of using the biological sound measuring device 1, a state is established where the pressure receiving portion 3a of the housing cover 32 comes into contact with the body surface S and the accommodation space SP1 is sealed by the body surface S via the housing cover 32 under a pressure from the body surface S.

When the pressure receiving portion 3a vibrates due to a pulmonary sound transmitted from the living body to the body surface S, an internal pressure of the accommodation space SP1 fluctuates due to this vibration, and an electrical signal corresponding to the pulmonary sound is measured by the sound measuring element M1 based on the fluctuation of the internal pressure.

The controller 4 illustrated in FIG. 1 determines whether or not a contact state and a contact position of the housing 31 with respect to the body surface S satisfy a condition necessary for measurement of the pulmonary sound, based on an intensity of a reflected sound measured by the sound measurer 36, and performs notification when it is determined that the condition is not satisfied.

For example, the controller 4 performs notification by causing the display unit 6 to display a message to prompt to change the way or position of pressing the pressure receiving portion 3a against the body surface S. The controller 4 may perform notification by outputting the message from a speaker (not illustrated).

The biological sound measuring device 1 may be configured to be connectable to, for example, a smartphone, and display or audio output of the message may be performed using a display or a speaker of the smartphone.

Here, output of the message is performed, but the present invention is not limited thereto. For example, a light emitting diode (LED) may be mounted on the biological sound measuring device 1, and the controller 4 may notify the user of whether the way and position of pressing are fine or not by causing the LED to emit, for example, blue light when it is determined that the condition is satisfied, and by causing the LED to emit, for example, red light when it is determined that the condition is not satisfied.

Even in such a case, by describing meaning of emission colors of the LED in a manual or the like attached to the biological sound measuring device 1, it is possible to prompt the user to change one or both of the way of pressing and the position of pressing.

Hereinafter, a specific example of a method for determining whether or not the condition is satisfied will be described.

Figure 5:
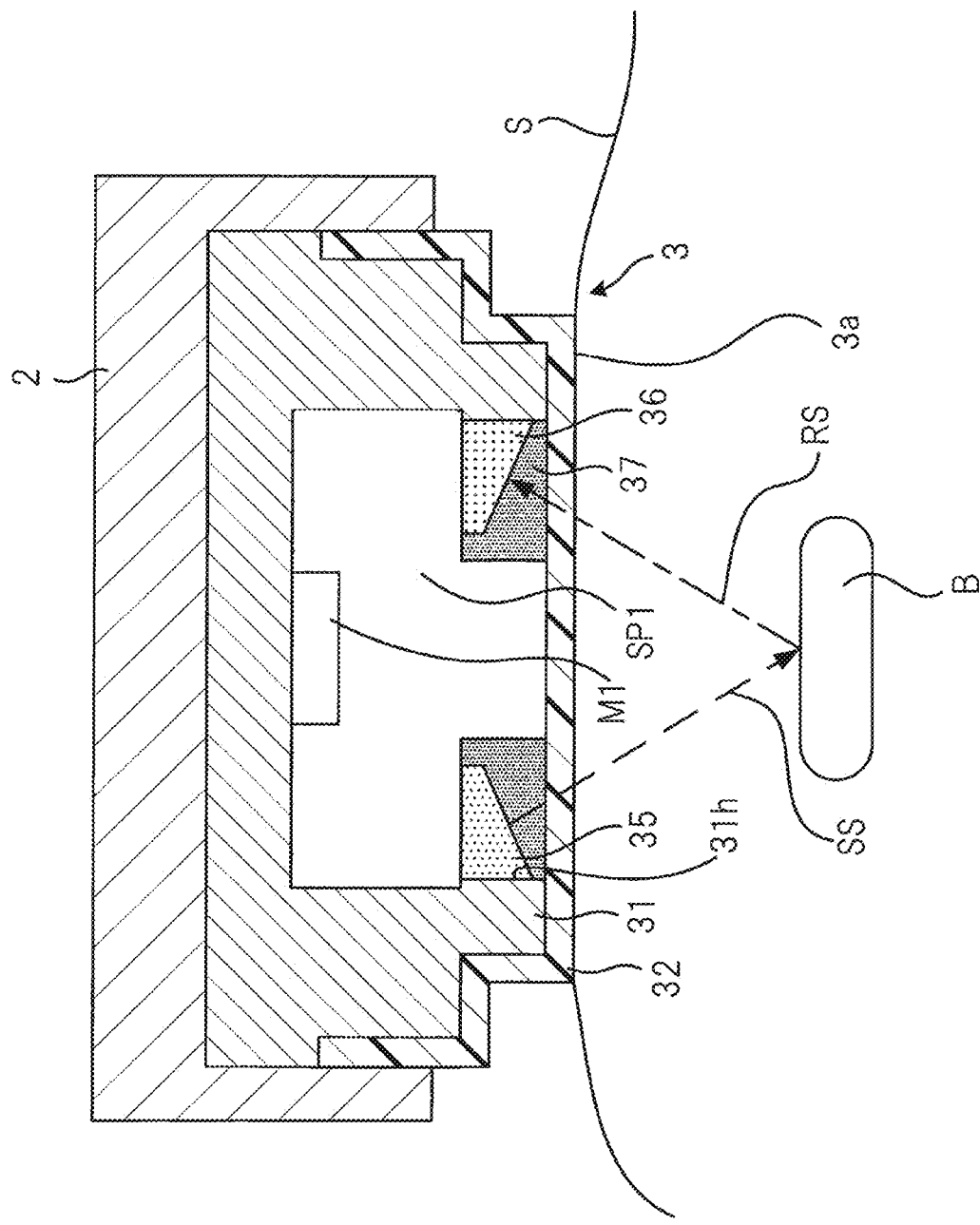
FIG. 5 is a schematic view illustrating a state where the measuring unit 3 of the biological sound measuring device 1 is pressed against a body surface S.

FIG. 5 is a schematic view illustrating a state where the measuring unit 3 of the biological sound measuring device 1 is pressed against the body surface S. FIG. 5 illustrates an example in which a bone B such as a rib or a sternum is present below the body surface S in contact with the pressure receiving portion 3a.

When the bone B is present below the accommodation space SP1 as illustrated in FIG. 5, since a pulmonary sound transmitted from below the bone B is reflected and diffracted by the bone B, an intensity of the pulmonary sound transmitted to the sound measuring element M1 is reduced. Therefore, it is difficult to accurately determine whether or not wheezing is included in the pulmonary sound.

In the state where the bone B is present below the accommodation space SP1 as described, a sound SS generated by the sound generator 35 is reflected by the bone B and becomes a reflected sound RS, and the reflected sound RS is measured by the sound measurer 36.

A distance from the body surface S assumed as a pressing place of the biological sound measuring device 1 to the bone B, is statistically known. In addition, acoustic impedance of the bone B is also statistically known. Accordingly, in the state where the bone B is present below the accommodation space SP1, it is possible to predict, in advance, time required from the time when the sound SS is generated to the time when the reflected sound RS of the sound SS is measured by the sound measurer 36, based on the known distance. In this state, based on an intensity of the sound SS and acoustic impedance of the bone B, it is possible to predict a degree of an intensity of the reflected sound RS with respect to the intensity of the sound SS.

Therefore, in a case where a difference between a generation timing of the sound SS and a measurement timing of the reflected sound RS of the sound SS measured by the sound measurer 36 is within a range (a range of time difference predicted in the case where the bone B is present) set in advance and the intensity of the reflected sound RS is within a range (a range of intensity predicted in the case where the bone B is present) set in advance, the controller 4 determines that the bone B is present below the accommodation space SP1 and that the contact position does not satisfy the above condition.

Figure 6:
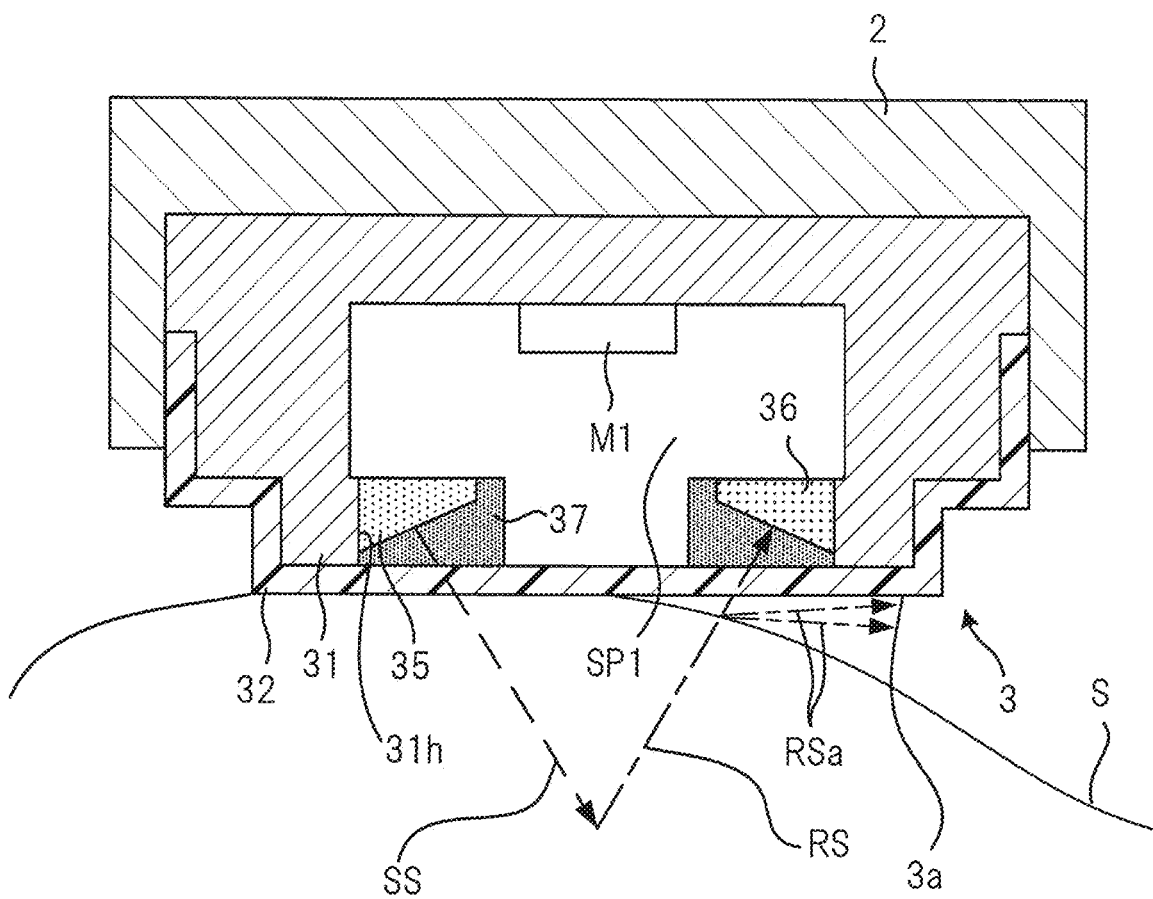
FIG. 6 is a schematic view illustrating a state where the measuring unit 3 of the biological sound measuring device 1 is pressed against the body surface S.

FIG. 6 is a schematic view illustrating a state where the measuring unit 3 of the biological sound measuring device 1 is pressed against the body surface S. FIG. 6 illustrates an example in which a part of the pressure receiving portion 3a is not in contact with the body surface S and sealing state of the accommodation space SP1 is incomplete.

In a state where the sealing is incomplete as illustrated in FIG. 6, since an external sound may be measured by the sound measuring element M1, it is difficult to accurately determine whether or not wheezing is included in the pulmonary sound. In this state, a part RSa of the reflected sound RS from the living body, of the sound SS generated by the sound generator 35 leaks to the outside, and the intensity of the reflected sound RS measured by the sound measurer 36 is lower than that in the case where the sealing state is complete. Further, even when the bone B is present as illustrated in FIG. 5 in the state where the sealing state is incomplete, the intensity of the reflected sound RS is lower than that in the case where the sealing of the accommodation space SP1 is complete.

When the sealing is complete and the bone B is not present below the pressure receiving portion 3a, the sound SS generated by the sound generator 35 reaches a deep part of the living body, and then is measured by the sound measurer 36 as the reflected sound RS. Therefore, in this case, the intensity of the reflected sound RS is greater than that in the case where the sealing state is incomplete and the bone B is present and that in the case where the sealing state is incomplete and the bone B is not present. The intensity of the reflected sound RS in the case where the sealing is complete and the bone B is present below the pressure receiving portion 3a is greater than that in the case where the sealing is complete and the bone B is not present below the pressure receiving portion 3a.

Therefore, when the intensity of the reflected sound RS measured by the sound measurer 36 is lower than a threshold set in advance (a lower limit value of the intensity of the reflected sound RS which is predicted in the case where the sealing is complete and the bone B is not present below the pressure receiving portion 3a), the controller 4 determines that the sealing of the accommodation space SP1 is incomplete and that the contact state does not satisfy the condition. Further, when the intensity of the reflected sound RS measured by the sound measurer 36 is equal to or greater than the threshold, the controller 4 determines that the sealing of the accommodation space SP1 is complete and that the contact state satisfies the condition.

(Operation Example of Biological Sound Measuring Device 1)

Figure 7:
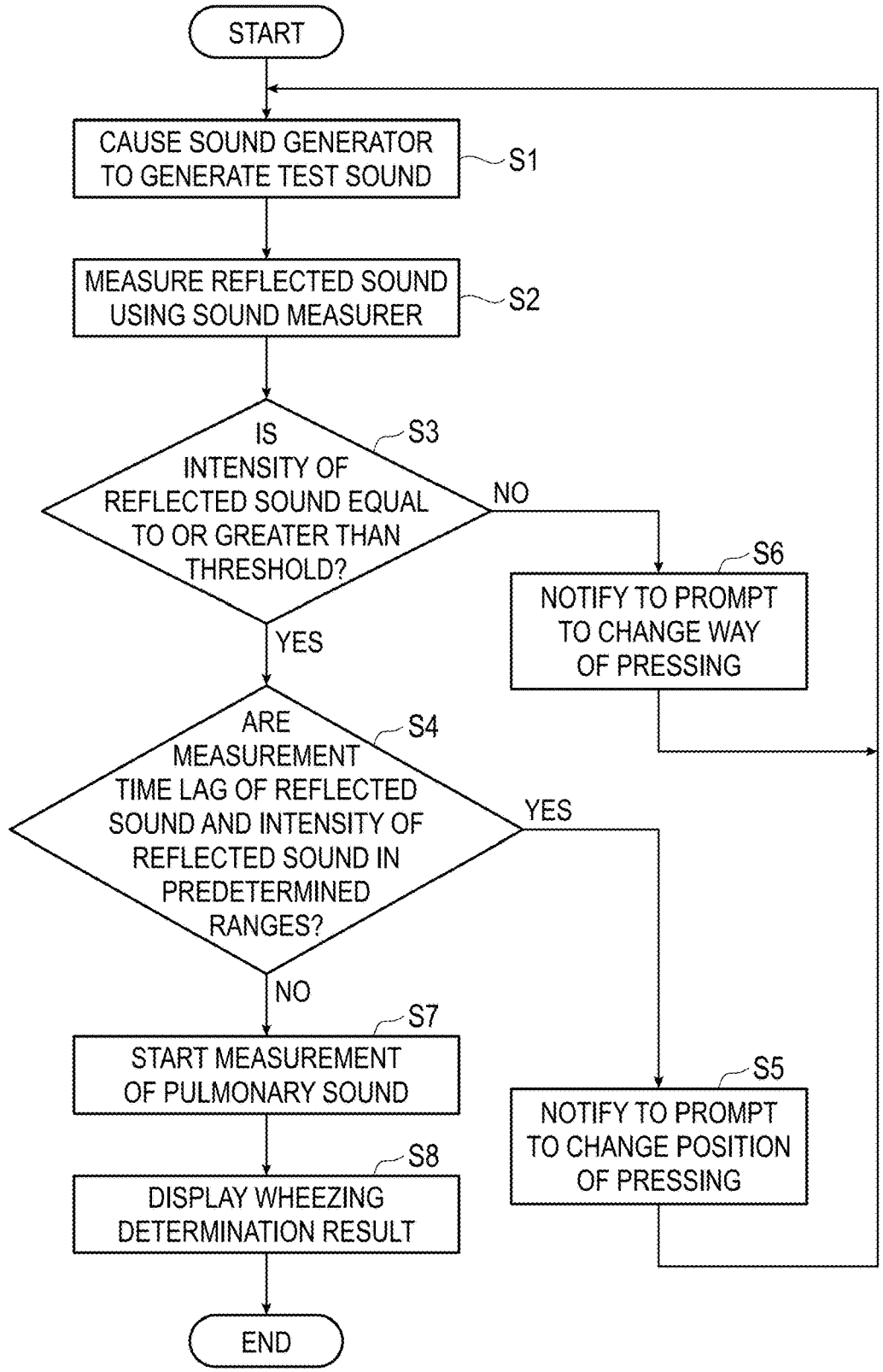
FIG. 7 is a flowchart for illustrating an operation example of the biological sound measuring device 1 illustrated in FIG. 1.

FIG. 7 is a flowchart for illustrating an operation example of the biological sound measuring device 1 illustrated in FIG. 1.

When the biological sound measuring device 1 is powered on, the controller 4 causes the sound generator 35 to generate a test sound of, for example, several MHz (step S1).

Further, the sound measurer 36 measures a reflected sound of the test sound generated by the sound generator 35 (step S2), and information on the reflected sound is input to the controller 4.

Next, the controller 4 determines whether or not an intensity of the reflected sound measured in step S2 is equal to or greater than the threshold (step S3).

When the intensity of the reflected sound is lower than the threshold (step S3: NO), the controller 4 determines that sealing state of the accommodation space SP1 is incomplete (a contact state does not satisfy the condition). Further, the controller 4 uses, for example, the display unit 6 to perform notification to prompt to change a way of pressing the measuring unit 3 against the body surface S (step S6). Through the processing of step S6, for example, a message such as "Please bring the head into close contact with your body" is displayed on the display unit 6. After step S6, the process returns to step S1.

When the intensity of the reflected sound is equal to or greater than the threshold (step S3: YES), the controller 4 obtains a difference between a generation timing of the test sound generated in step S1 and a measurement timing of the reflected sound measured in step S2, and the controller 4 determines whether the difference is within the range set in advance and the intensity of the reflected sound measured in step S2 is within the range set in advance (step S4).

When the determination in step S4 is YES, the controller 4 determines that a bone is present below the accommodation space SP1 (a contact position does not satisfy the condition), and uses, for example, the display unit 6 to perform notification to prompt to change a position of pressing the measuring unit 3 against the body surface S (step S5).

Through the processing of step S5, for example, a message such as "Please shift the position where the head is pressed" is displayed on the display unit 6. After step S5, the process returns to step S1.

When the determination in step S4 is NO (specifically, when the difference between the generation timing of the test sound and the measurement timing of the reflected sound is greater than a predicted value or when the intensity of the reflected sound measured in step S2 is outside the range set in advance), the controller 4 determines that sealing state of the accommodation space SP1 is complete and that no bone is present below the accommodation space SP1 (the contact state and the contact position satisfy the condition). Further, the controller 4 starts measurement of pulmonary sound using the sound measuring element M1 (step S7).

Specifically, of information on sounds of 10 Hz to 10 kHz to be measured by the sound measuring element M1, the controller 4 stores, in the RAM, information on sounds in a predetermined frequency range of pulmonary sound (10 Hz to 1.5 kHz) as information on pulmonary sound. Further, when information on pulmonary sounds over a certain period is stored in the RAM, the controller 4 analyzes the information to determine presence or absence of wheezing, displays a determination result on, for example, the display unit 6 (step S8), and ends the measurement.

(Effects of Biological Sound Measuring Device 1)

As described above, according to the biological sound measuring device 1, by measuring the reflected sound of the test sound generated by the sound generator 35 with the sound measurer 36 and by analyzing the reflected sound, it is possible to determine with high accuracy whether or not any of the contact state and the contact position of the housing 31 with respect to the body surface S satisfies the condition.

The sound generator 35 and the sound measurer 36 are disposed in the accommodation space SP1 that can be sealed by the body surface S. Therefore, even when the pressure receiving portion 3a is slightly floated as illustrated in FIG. 6, this state can be accurately detected based on a decrease in the intensity of the reflected sound due to sound leakage. As described above, according to the biological sound measuring device 1, it is possible to accurately determine the contact state and to support highly accurate measurement of the pulmonary sound, as compared with a related-art method of determining the contact state using a photodetector or a contact sensor.

According to the biological sound measuring device 1, in a case where there is a bone below the accommodation space SP1, it is possible to determine whether or not the bone is present based on the reflected sound reflected by the bone. Therefore, as compared with a related-art method of simply measuring a sound to determine whether or not the contact position is good, it is possible to improve the determination accuracy.

According to the biological sound measuring device 1, the sound generating surface 35a of the sound generator 35 and the sound measuring surface 36a of the sound measurer 36 are both inclined, and a direction which the sound generating surface 35a faces and a direction which the sound measuring surface 36a faces intersect with each other. Therefore, a sound generated by the sound generator 35 can be efficiently guided to the bone inside the living body, and a reflected sound of the sound can be efficiently guided to the sound measurer 36. Therefore, it is possible to determine with high accuracy whether or not the contact position satisfies the condition.

It is not essential that the sound generating surface 35a of the sound generator 35 and the sound measuring surface 36a of the sound measurer 36 are inclined. For example, the sound generating surface 35a of the sound generator 35 and the sound measuring surface 36a of the sound measurer 36 may be surfaces perpendicular to the pressing direction.

(Modification of Biological Sound Measuring Device 1)

In a case where the sound generator 35 and the sound measurer 36 are configured with an ultrasonic transducer in the biological sound measuring device 1, the sound generator 35 may function as a sound measurer that measures a sound, and the sound measurer 36 may function as a sound generator that generates a sound.

For example, after a test sound is generated by the sound generator 35 and a reflected sound thereof is measured by the sound measurer 36, a test sound may be generated by the sound measurer 36 and a reflected sound of the test sound may be measured by the sound generator 35.

As described above, the test sound is generated multiple times with traveling directions changed, and the determination in step S3 and step S4 in FIG. 7 is performed based on a relationship between the respective test sounds and the reflected sounds thereof, so that it is possible to determine with far higher accuracy whether or not the contact position and the contact state satisfy the condition.

In a case where the sound generator 35 is configured with an ultrasonic transducer, the sound measurer 36 may be replaced with the sound generator 35.

Figure 8:
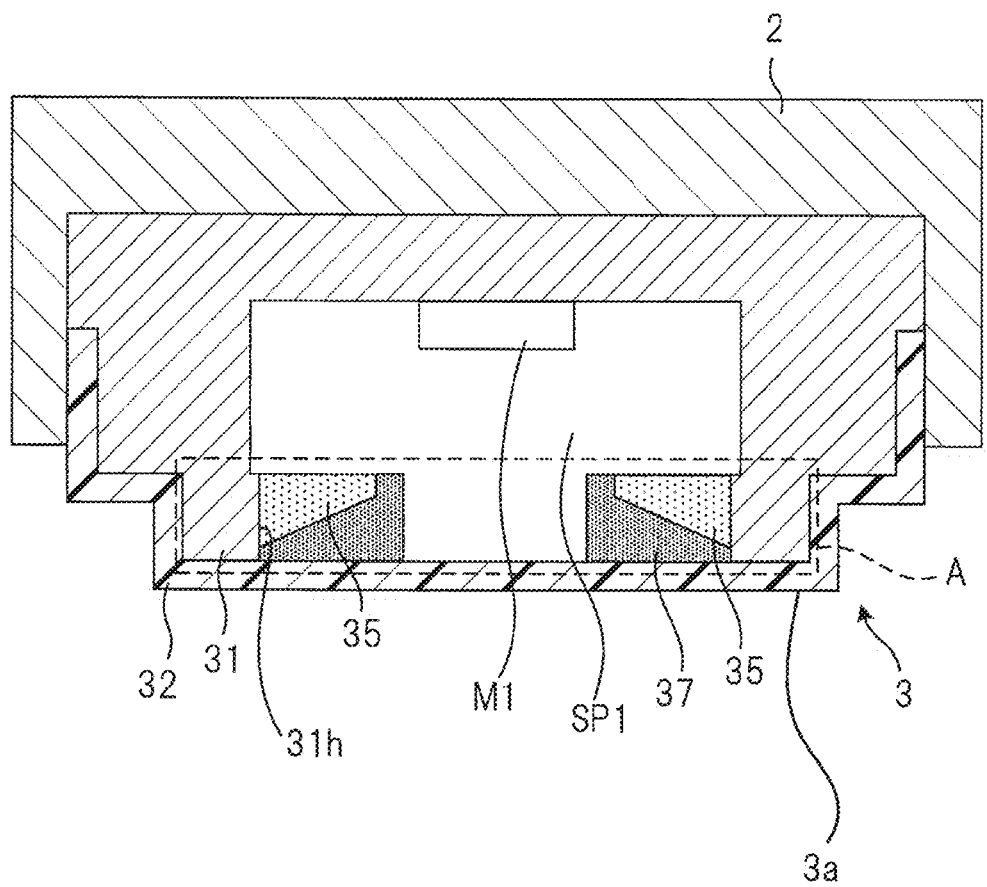
FIG. 8 is a view illustrating a cross section of the measuring unit 3 as a modification.
Figure 9:
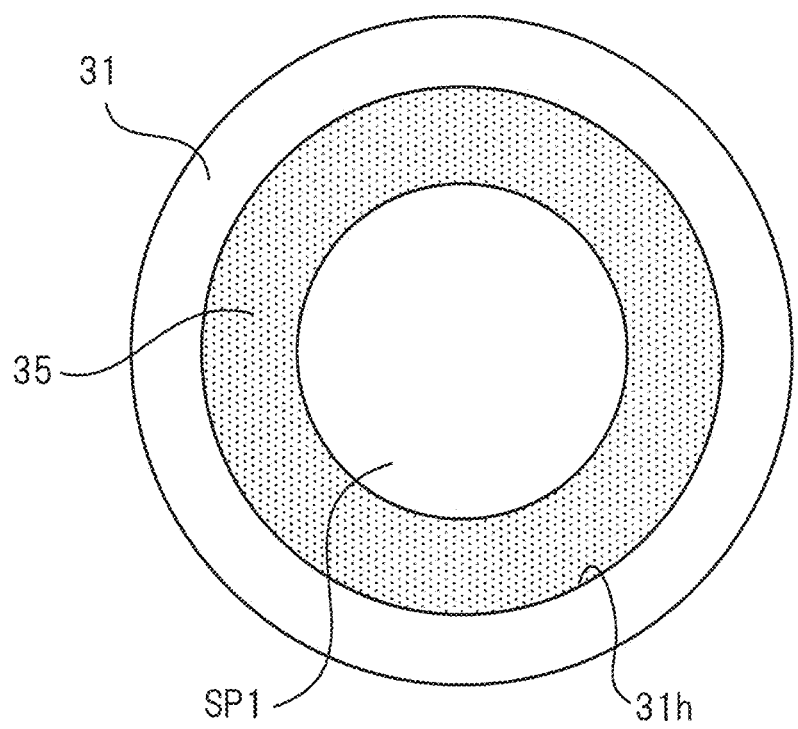
FIG. 9 is a view of a range A of the measuring unit 3 illustrated in FIG. 8 as viewed from a pressing direction, in which illustration of the acoustic impedance matching layer 37 is omitted.

FIG. 8 is a view illustrating a cross section of the measuring unit 3 as a modification. FIG. 9 is a view of a range A of the measuring unit 3 illustrated in FIG. 8 as viewed from the pressing direction, in which illustration of the acoustic impedance matching layer 37 is omitted.

As illustrated in FIG. 9, the sound generator 35 of the measuring unit 3 according to the modification illustrated in FIG. 8 has an annular planar shape. In the measuring unit 3 illustrated in FIG. 8, after the sound generator 35 generates a test sound, the sound generator 35 measures a reflected sound of the test sound. That is, the sound generator 35 also functions as a sound measurer. According to this configuration, the test sound can be applied to a bone from various directions in a single time of generation of the test sound, and the contact position and the contact state can be determined at a high speed and with high accuracy.

In the biological sound measuring device 1, the sound measuring element M1 may be configured to measure a sound (several MHz) generated by the sound generator 35, in addition to sounds in a frequency range (for example, 10 Hz to 10 kHz) including a frequency range of pulmonary sound.

In this case, the sound measurer 36 is not necessary, and the sound measuring element M1 functions as a sound measurer. In this configuration, for example, the sound measurer 36 may be replaced with the sound generator 35 as illustrated in FIGS. 8 and 9.

As described above, in the configuration in which the sound measuring element M1 can measure the sound generated by the sound generator 35, the sound measuring element M1 may measure the reflected sound in step S2 of FIG. 7.

According to this configuration, the sound measurer 36 is not necessary, and as illustrated in FIG. 9, the sound generator 35 may be annular. Therefore, the test sound can be applied to a bone from various directions in a single time of generation of the test sound, and the contact position and the contact state can be determined at a high speed and with high accuracy.

Although the measurement of pulmonary sound is started when both the contact position and the contact state satisfy the condition in the above description, and the controller 4 may start the measurement of pulmonary sound when one of the contact position and the contact state satisfies the condition. An operation in this case will be described below.

Figure 10:
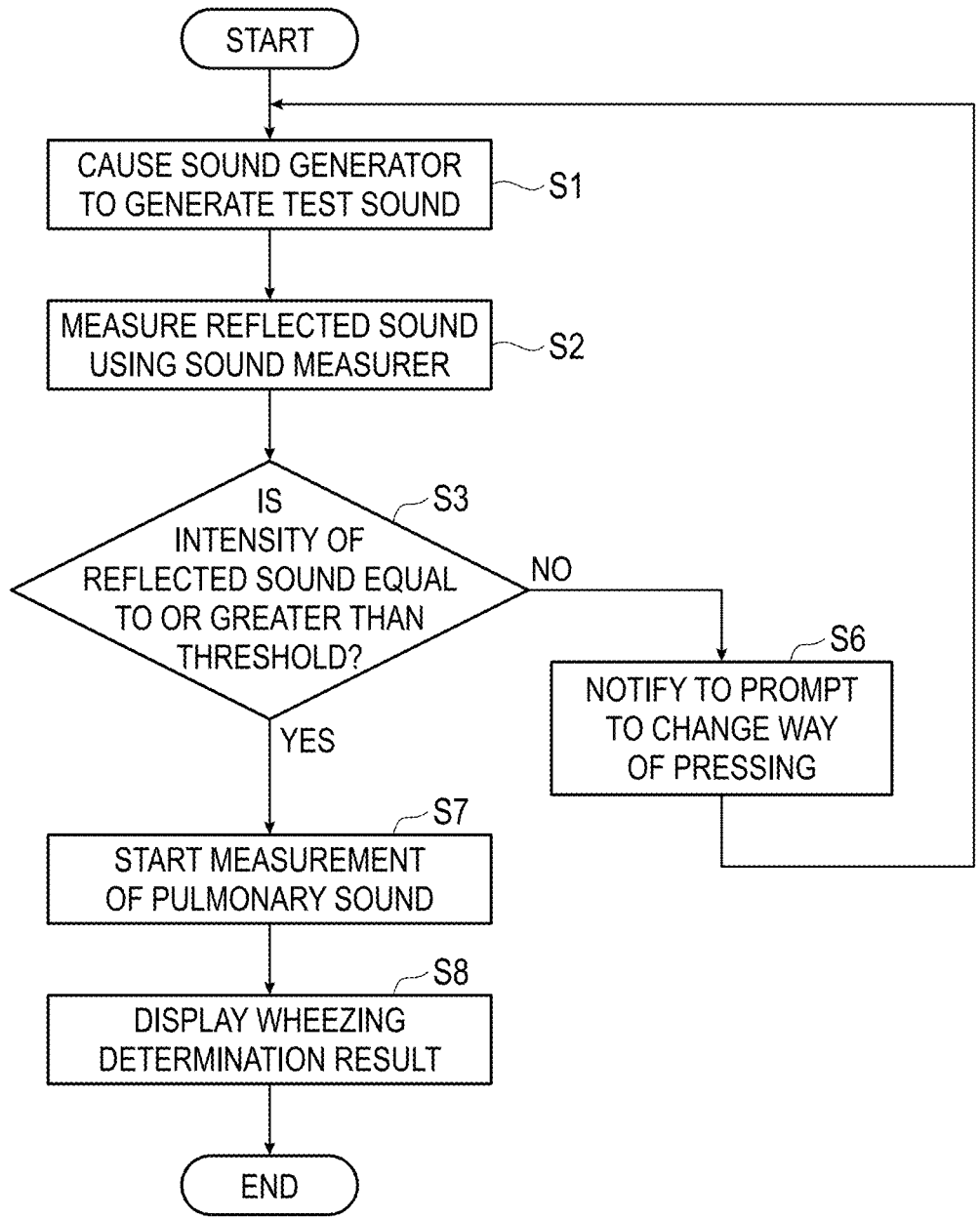
FIG. 10 is a flowchart for illustrating a first modification of an operation of the biological sound measuring device 1.

FIG. 10 is a flowchart for illustrating a first modification of an operation of the biological sound measuring device 1. In FIG. 10, the same processes as those in FIG. 7 are denoted by the same reference signs.

The flowchart illustrated in FIG. 10 is the same as the flowchart of FIG. 7 except that step S4 and step S5 are deleted and that the processing of step S7 is performed when the determination in step S3 is YES. When the determination in step S3 of FIG. 10 is NO, the controller 4 determines that the contact state does not satisfy the condition, and performs the processing of step S6. When the determination in step S3 of FIG. 10 is YES, the controller 4 determines that the contact state satisfies the condition, and performs the processing of step S7.

According to the operation of the first modification illustrated in FIG. 10, the measurement of pulmonary sound can be started in a state where the contact state satisfies the condition, and highly accurate measurement of the pulmonary sound can be supported.

Figure 11:
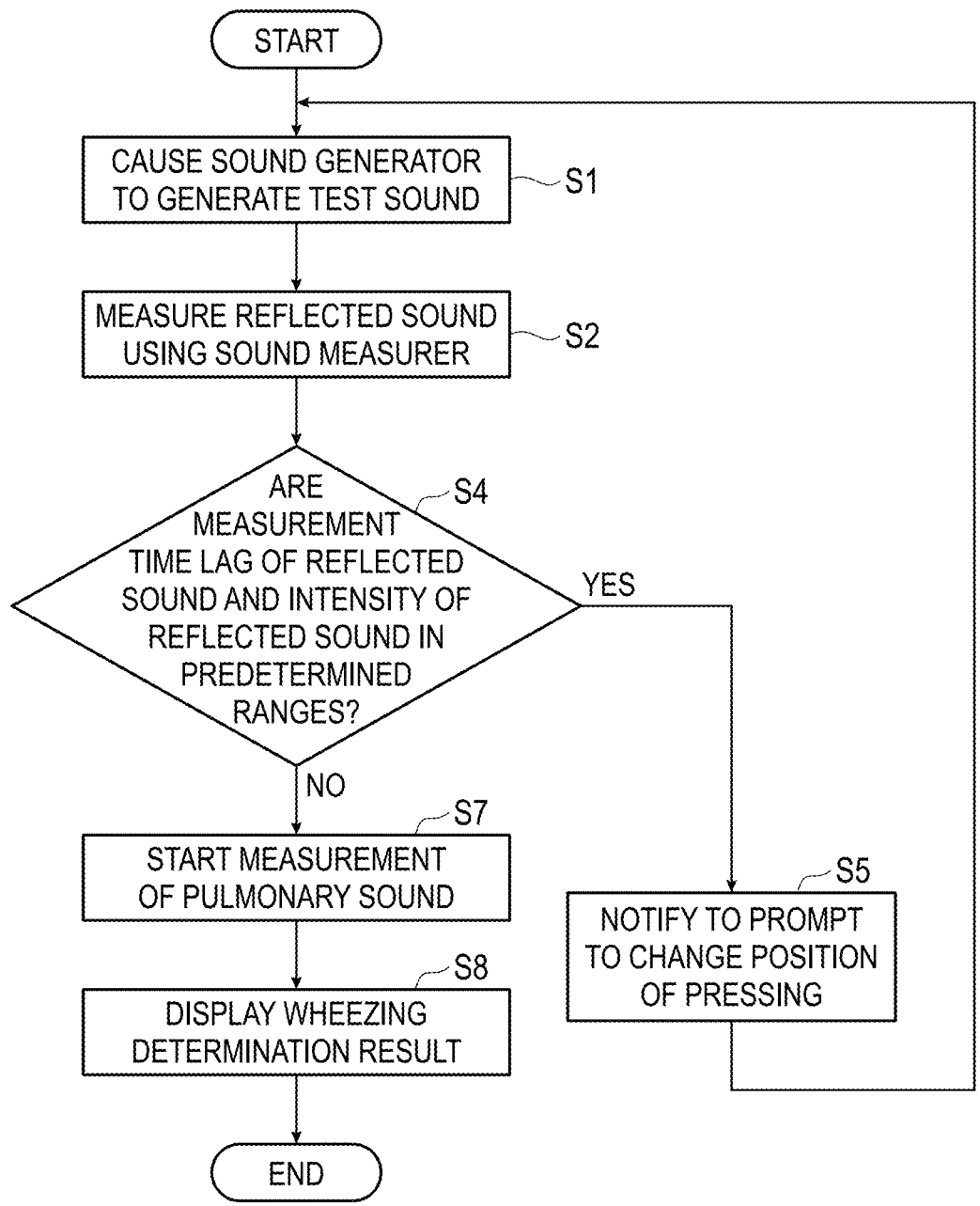
FIG. 11 is a flowchart for illustrating a second modification of the operation of the biological sound measuring device 1.

FIG. 11 is a flowchart for illustrating a second modification of the operation of the biological sound measuring device 1. In FIG. 11, the same processes as those in FIG. 7 are denoted by the same reference signs.

The flowchart illustrated in FIG. 11 is the same as the flowchart of FIG. 7 except that step S3 and step S6 are deleted and that step S4 is performed following step S2.

When the determination in step S4 of FIG. 11 is YES, the controller 4 determines that the contact position does not satisfy the condition, and performs the processing of step S5. When the determination in step S4 of FIG. 11 is NO, the controller 4 determines that the contact position satisfies the condition, and performs the processing of step S7.

According to the operation of the second modification illustrated in FIG. 11, the measurement of pulmonary sound can be started in a state where the contact position satisfies the condition, and highly accurate measurement of the pulmonary sound can be supported.

Although an embodiment of the present invention and modifications thereof have been described above, the present invention is not limited thereto, and can be modified as appropriate. For example, although the sound measuring element M1 is configured to measure a pulmonary sound as a biological sound in the embodiment and the modifications described above, the sound measuring element M1 may be configured to measure a cardiac sound or the like as a biological sound.

Although the embodiments are described above with reference to the drawings, it is needless to say that the present invention is not limited to such examples. It will be apparent to those skilled in the art that various changes and modifications may be conceived within the scope of the claims. It is also understood that the various changes and modifications belong to the technical scope of the present invention. Components in the embodiments described above may be combined freely within a range not departing from the spirit of the present invention.

What is claimed is:

1. A biological sound measuring device to measure a biological sound of a living body, the biological sound measuring device comprising:
    a housing which defines an accommodation space to be sealed by a body surface of the living body in a state of being pressed against the body surface;
    a housing cover that closes the accommodation space and covers the housing;
    a first ultrasonic transducer that is disposed in the accommodation space of the housing and that generates a sound toward the body surface;
    a second ultrasonic transducer that is disposed in the accommodation space of the housing and that measures a reflected sound of the sound generated by the first ultrasonic transducer; and
    a controller that determines whether or not a contact state of the housing with respect to the body surface satisfies a first condition necessary for measurement of the biological sound and/or whether or not a contact position of the housing with respect to the body surface satisfies a second condition necessary for measurement of the biological sound, based on the reflected sound measured by the second ultrasonic transducer, and that performs notification when it is determined that the first condition or the second condition is not satisfied; wherein
    the notification provides a suggestion for satisfying the first condition or the second condition;
    the accommodation space is configured to be sealed by the body surface via the body surface pressing against the housing cover;
    the biological sound of the living body is measured based on pressure fluctuation in the accommodation space; and
    when a difference between a generation timing of the sound by the first ultrasonic transducer and a measurement timing of the reflected sound of the sound which is measured by the second ultrasonic transducer is within a first range and an intensity of the reflected sound is within a second range whose lower limit is equal to or greater than a threshold set in advance, the controller determines that the contact position does not satisfy the second condition.

2. The biological sound measuring device according to claim 1,
    wherein when an intensity of the reflected sound measured by the second ultrasonic transducer is lower than a threshold set in advance, the controller determines that the contact state does not satisfy the first condition.

3. The biological sound measuring device according to claim 1,
    wherein when the difference between the generation timing of the sound by the first ultrasonic transducer and the measurement timing of the reflected sound of the sound which is measured by the second ultrasonic transducer is outside the first range, the controller determines that the contact position satisfies the second condition.

4. The biological sound measuring device according to claim 1, further comprising:
    a microphone that is disposed in the accommodation space of the housing and that measures a sound in a frequency range lower than a frequency range of the sound generated by the first ultrasonic transducer,
    wherein when it is determined that at least one of the first and second conditions is satisfied, the controller stores, as the biological sound, a sound in a predetermined frequency range of sounds that are measured by the microphone.

5. The biological sound measuring device according to claim 4,
    wherein the predetermined frequency range is 10 Hz or more and 1.5 kHz or less.

6. The biological sound measuring device according to claim 1,
    wherein the second ultrasonic transducer measures the sound generated by the first ultrasonic transducer and a sound in a frequency range lower than a frequency range of the sound generated by the first ultrasonic transducer, and
    wherein when it is determined that at least one of the first and second conditions is satisfied, the controller stores, as the biological sound, a sound that is different from the sound generated by the first ultrasonic transducer and that is in a predetermined frequency range of sounds that are measured by the second ultrasonic transducer.

7. The biological sound measuring device according to claim 6,
wherein the predetermined frequency range is 10 Hz or more and 1.5 kHz or less.

8. The biological sound measuring device according to claim 1,
wherein the first ultrasonic transducer is formed along an inner wall that defines the accommodation space of the housing, and
wherein a sound generating surface of the first ultrasonic transducer is inclined in a direction away from the body surface with respect to a plane perpendicular to a pressing direction of the housing.

9. A biological sound measurement support method for supporting measurement of a biological sound of a living body performed by a biological sound measuring device,
the biological sound measuring device including: a housing that defines an accommodation space to be sealed by a body surface of the living body in a state of being pressed against the body surface; a housing cover that closes the accommodation space and covers the housing; a first ultrasonic transducer that is disposed in the accommodation space of the housing and that generates a sound toward the body surface; and a second ultrasonic transducer that is disposed in the accommodation space of the housing and that measures a reflected sound of the sound generated by the first ultrasonic transducer, and the biological sound measuring device measuring the biological sound of the living body based on pressure fluctuation in the accommodation space,
the biological sound measurement support method comprising:
the steps of determining whether or not a contact state of the housing with respect to the body surface satisfies a first condition necessary for measurement of the biological sound and/or whether or not a contact position of the housing with respect to the body surface satisfies a second condition necessary for measurement of the biological sound, based on the reflected sound measured by the second ultrasonic transducer, and performing notification when it is determined that the first condition or the second condition is not satisfied; wherein
the notification provides a suggestion for satisfying the first condition or the second condition;
the accommodation space is sealed by the body surface via the body surface pressing against the housing cover;
in response to a difference between a generation timing of the sound by the first ultrasonic transducer and a measurement timing of the reflected sound of the sound which is measured by the second ultrasonic transducer being within a first range and an intensity of the reflected sound being within a second range whose lower limit is equal to or greater than a threshold set in advance, determining that the contact position does not satisfy the second condition, and
wherein in response to the difference between the generation timing of the sound by the first ultrasonic transducer and the measurement timing of the reflected sound of the sound which is measured by the second ultrasonic transducer being outside the first range, determining that the contact position satisfies the second condition.

10. A non-transitory computer-readable storage medium which stores a biological sound measurement support program for supporting measurement of a biological sound of a living body performed by a biological sound measuring device,
the biological sound measuring device including: a housing that defines an accommodation space to be sealed by a body surface of the living body in a state of being pressed against the body surface; a housing cover that closes the accommodation space and covers the housing; a first ultrasonic transducer that is disposed in the accommodation space of the housing and that generates a sound toward the body surface; and a second ultrasonic transducer that is disposed in the accommodation space of the housing and that measures a reflected sound of the sound generated by the first ultrasonic transducer, and the biological sound measuring device measuring the biological sound of the living body based on pressure fluctuation in the accommodation space,
the biological sound measurement support program causing a computer to perform the steps of:
determining whether or not a contact state of the housing with respect to the body surface satisfies a first condition necessary for measurement of the biological sound and/or whether or not a contact position of the housing with respect to the body surface satisfies a second condition necessary for measurement of the biological sound, based on the reflected sound measured by the second ultrasonic transducer, and performing notification when it is determined that the first condition or the second condition is not satisfied; wherein
the notification provides a suggestion for satisfying the first condition or the second condition;
the accommodation space is configured to be sealed by the body surface via the body surface pressing against the housing cover; and
wherein when a difference between a generation timing of the sound by the first ultrasonic transducer and a measurement timing of the reflected sound of the sound which is measured by the second ultrasonic transducer is within a first range and an intensity of the reflected sound is within a second range whose lower limit is equal to or greater than a threshold set in advance, the computer determines that the contact position does not satisfy the second condition.

* * * * *